(12) United States Patent
Mirzaee

(10) Patent No.: US 7,754,244 B2
(45) Date of Patent: Jul. 13, 2010

(54) COMPOSITIONS AND METHODS FOR TREATING OR PREVENTING HAIR LOSS AND PROCESSES FOR MAKING THE SAME

(76) Inventor: Fatemeh Mirzaee, 17 Taghavi-Shirazi, Tehran, Iran (IR) 19159

( * ) Notice: Subject to any disclaimer, the term of this patent is extended or adjusted under 35 U.S.C. 154(b) by 0 days.

(21) Appl. No.: 11/716,178

(22) Filed: Mar. 9, 2007

(65) Prior Publication Data
US 2008/0220082 A1    Sep. 11, 2008

(51) Int. Cl.
*A61K 35/32* (2006.01)
(52) U.S. Cl. .................................................. 424/549
(58) Field of Classification Search ............... None
See application file for complete search history.

(56) References Cited

U.S. PATENT DOCUMENTS 4,701,471 A * 10/1987 Loucks et al. ............... 514/784
6,019,976 A *  2/2000 Bryant ....................... 424/727
6,149,932 A * 11/2000 Allen ......................... 424/439

OTHER PUBLICATIONS

Miller et al., Journal of food Science, 1982, vol. 47, p. 657-660.*
Cordain et al., European journal of Clinical Nutrition, 2002, vol. 56, p. 181-191.*
Meisnest, F.H., Oil & Fat Industries, 1928, vol. V, No. 2, p. 33-45.*
Liang & Liao, Biochem J, 1992, vol. 258, p. 557-562.*
Church & Lyman, Journal of Archaeological Science, 2003, vol. 30, p. 1077-1084.*
Mello et al., Journal of Food Science, 1976, vol. 41, p. 226-230.*
Skolnik et al., Arch Dermatol. 1977, vol. 113, No. 7, p. 939-941.*
Liang et al., J. Invest. Dermatol., 1997, vol. 109, p. 152-157.*

* cited by examiner

*Primary Examiner*—L Blaine Lankford
*Assistant Examiner*—Kade Ariani
(74) *Attorney, Agent, or Firm*—Barry Choobin; Choobin & Choobin Consultancy L.L.C.

(57) ABSTRACT

The present invention relates to composition useful in growing hair. The compositions are particularly suited for re-growing hair in subjects who have experienced hair loss due to any cause. The compositions comprise essentially the lipoidic fraction of mammalian bone marrow. Methods of using the compositions and processes of preparing the lipoidic fraction for the compositions are also disclosed.

11 Claims, No Drawings

COMPOSITIONS AND METHODS FOR TREATING OR PREVENTING HAIR LOSS AND PROCESSES FOR MAKING THE SAME

FIELD OF THE INVENTION

The present invention relates primarily to methods and compositions for promoting hair growth, or of preventing or minimizing hair loss. Also disclosed are processes for preparing the compositions.

The methods include topical application of the compositions to the hair follicles, or skin, in need of treatment. The compositions include as the essential component the lipoidic fraction of animal bone marrow. Processes for obtaining this fraction include the simmering of animal bones containing marrow in water for extended periods of time, during which the oily fraction is collected periodically.

BACKGROUND OF THE INVENTION

There are various causes of hair loss in mammals, specifically humans. The most ususal type of hair loss is commonly referred to as male-pattern baldness, which is associated with genetic factors that in time lead to the hair follicles on the scalp exhibiting an increased sensitivity to the dihydrotestosterone (DHT). The enzyme 5-α-reductase produced by the hair follicles reacts with the male hormone testosterone, also present in the follicles, to produce DHT. Consequently, hair follicle receptors that are sensitive to DHT respond by shrinking to the point in which they no longer produce visible hair.

Other causes of hair loss include physical and emotional stress, hormonal disturbances, certain medications, and various underlying diseases, for instance thyroid conditions and diabetes.

For years, the cosmetics industry has been developing compositions, methods and devices to prevent hair loss and/or promote hair growth. Such remedies typically focus on increasing blood supply to the scalp, removing sebum in the scalp to prevent clogging of the pores, and/or increasing nutrition to the hair root to reduce hair loss and promote hair growth. None of the available cosmetic or over-the-counter remedies, however, provides a comprehensive treatment that is effective to address all of the various factors that may be contributing to hair loss in the affected population.

The pharmaceutical and nutraceutical industries have also attempted to provide comprehensive topical and/or oral treatments that promote hair re-growth and/or prevent further hair loss. In the pharmaceutical arena, the US Food & Drug Administration has approved two drugs it considers "safe and effective". One of these, minoxidil, marketed as Rogaine®, causes hair growth when applied to the scalp and slows the rate of hair loss in some individuals by stimulating hair follicles. The other, finasteride, marketed as Propecia®, is a drug that is taken orally to treat androgenic alopecia by blocking the formation of DHT. However, there are adverse side effect with both of these pharmaceuticals. Minoxidil may cause low blood pressure, increase in heart rate, cause weight gain due to water retention, and the scalp may become inflamed. Finasteride may cause genital deformities in male infants, impotence, decreased libido, and genital deformities in male infants, in addition to hives, rash, and swelling.

While the industry and literature are replete with reports of various methods, devices and formulations for promoting hair growth and/or preventing hair loss, for the most part the available strategies of the prior art have not been very successful in providing hair growth, particularly in alopecia and male-pattern baldness situations. Moreover, pharmaceutical formulations, while apparently having the most success, have undesirable side effects that lessen their attractiveness to users.

As such, a need exists for a remedy for hair loss due to a variety of causes and that is not only effective in promoting hair growth, but is also safe and does not have adverse side effects. The present invention, for the first time, provides a product that prevents hair loss and promotes new hair growth in a safe, effective and natural manner.

SUMMARY OF THE INVENTION

The present intention relates to compositions and methods for treating hair loss. As a favorable adjunctive effect, the compositions have also been found to be useful in conditioning the hair shaft, providing body and manageability to the hair.

As the invention relates to treatment of hair loss, its effects include promoting hair growth in general and, in particular, promoting the growth of hair in cases of alopecia due to any cause, including male-pattern baldness, promoting the growth in hair transplants, preventing or minimizing hair loss, reducing and/or preventing hair loss as a result of chemotherapy, and thickening the hair, including the eyebrows and eyelashes.

It is the principal object of the present invention to provide compositions for reducing hair loss and promoting hair growth as a comprehensive treatment for a plurality of known and/or suspected causes of hair loss, and a process of preparing the same. The hair growth compositions of the invention are natural and non-toxic.

The compositions are composed of the lipoidic fraction of mammalian bone marrow, which is obtainable through boiling and simmering mammalian bones in aqueous solution for a certain time during which the oil fraction is recovered periodically. The compositions contain only the oil fraction, and no water, and thus have the advantage of a long shelf-life on the order of about 5 years.

Another object of the present invention is to provide a method for regrowing hair, which generally comprised administering an effective amount of the bone marrow oil composition to a subject. The subject is typically a human, although the compositions can be used in other mammals, for instance household pets. The administration is a topical application to a site where hair is desired to be regrown (or loss prevented). Typically, this site is the scalp or the eyebrows or eyelashes, i.e. terminal hair locations. Also, while the application for hair growth/loss prevention is topical, the compositions of the invention are safe enough to ingest (although not known to be effective for the purposes stated herein).

Another object of the invention is to provide a process for preparing the composition. The process is a simple yet elegant way to obtain the lipoidic fraction from the bone marrow that has the advantageous effects.

As an added benefit of the compositions disclosed herein, they also are useful as hair conditioners or styling products, in that they condition the hair shafts providing strength, shine, manageability and body to the hair.

The methods and products of the present invention have been found to be surprisingly effective in the treatment of hair loss. Additional objects and advantages of the invention are made apparent in the following detailed description.

DETAILED DESCRIPTION OF THE INVENTION

Humans have two types of hair, "terminal" hair which is longer, coarser and pigmented on the scalp, eyebrows and eyelashes and "vellus" hair which is soft, rarely more than 2 mm long and generally non- or lighter-pigmented.

Terminal hair is developed hair, which is generally longer, coarser, thicker, and darker than the shorter and finer vellus hair. Phases of growth in terminal hair are more apparent than in vellus hair; terminal hair generally has a longer anagen phase. A terminal hair has associated sebaceous glands, whereas a vellus hair may not. It's deep rooted and closer to the nourishment from the blood supply. The terminal hair also remains in the anagen stage much longer than vellus hair. At any one time, about 10 percent of the hair on the scalp is in a resting phase. After 2 to 3 months, the resting hair falls out and new hair starts to grow in its place. This growing phase lasts for 2 to 6 years. Abbot 90 percent of the hair on your scalp is growing at any one time. It is normal to shed some hair each day as part of this cycle. However, some people may experience excessive (more than normal) hair loss.

Individual hairs alternate periods of growth and dormancy. During the growth portion of the cycle (the anagen phase), hair follicles are long and bulbous, and the hair advances outward at about a third of a millimeter per day. After three to six months, body hair growth stops. The follicle shrinks and the root of the hair grows rigid. Following a period of dormancy, another growth cycle starts, and eventually a new hair pushes the old one out of the follicle from beneath. Head hair, by comparison, grows for a long duration and to a greater length before being shed. The rate of growth is approximately half an inch pet month.

Hair follicles are sensitive to internal and external changes, which may cause hair loss. Certain factors like changes in diet, stress level, drugs, health, and environment may result in hair loss, which is usually temporary snd ewill resolve over time or once the underlying cause is corrected. Usually, with hair loss the terminal hairs regress to vellus-type hairs in which the hair follicle reduces in size thereby producing smaller, finer hair. The shallowly rooted vellus hair, due to a shorter life cycle, does not get the chance to mature into deep-rooted terminal hair. Under other conditions, such as male pattern baldness, terminal hairs may revert to a vellus-like state.

At its essence, the composition of the invention is the oil fraction that is obtained by boiling and simmering the cleaned bones of mammals in water. This lipoidic fraction rises to the top during such a process, and usually is discarded when one is making a soup for consumption. However, for the present invention, this is the essential component.

The specific mechanism by which the compositions of the present invention are effective for treating such hair loss is not precisely known. In any case, the compositions have been shown to regrow terminal hair that has been lost, or become vellus hair-like. Restoration of overplucked or thinning eyebrows, for example, has also been accomplished with the present compositions. The hair re-growth effects are initially observed in a matter of days (about 10-14 days or so) with daily treatment.

It is noted that there is a commercial skincare product that claims to contain "bone marrow oil"; however, there is no description of how this component of the skin cream is produced (and so, exactly what it is), and there is no disclosure or suggestion of using the skincare product for hair or hair growth. See www.chicet.com, Chicet Natural European Skin Care Products, Los Angeles, Calif. Thus, the present invention for the first time describes a process for the manufacture of what will be referred to herein as "bone marrow oil", as well as discloses its surprising effects on hair growth promotion/hair loss prevention and other beneficial effects.

As the mammals from which the bones may be derived, the only limitation is that the mammals have hair or fur (thus excluding, for instance, sea mammals). Further, it is desirable to obtain the bones from mammals that are domesticated, simply for their ready availability and the best assurances of not being diseased (for instance by mammalian prion diseases). Preferably, the bones are obtained from a reputable butcher or the like, for ready availability and inherent safety measures taken by such.

The bones of the mammal are of any origin of the body, though preferably they are bones that contain the most marrow (for instance, leg and thigh bones, hip bones, etc.). The bones are first thoroughly rinsed and cleaned of all external matter, i.e. cartilage, meat, tendons and the like.

Next, the bones are broken crosswise or lengthwise to expose the marrow, and then placed in a container and covered with water in an amount sufficient to completely cover the bones and allowing for at least a few inches of water above that. Such a level of water is maintained throughout the rest of the process by adding water when needed.

The water is heated to the boiling stage, and then lowered to a simmer for an overall period of approximately 30 hours. During this simmering period, after at least about 5 hours, the oil that appears on the top of the container is skimmed off in a manner to obtain only the oil without any, or minimal water. It is essential to exclude the water in order to ultimately obtain a composition that will hot become contaminated with microbes and thus decompose. The oil phase obtained at this time point consitutes about 40-50% of the yield of the product from the bones.

After first skimming at the time point above, during the remaining simmering time (about an additional 25 hours), the oil fraction is skimmed off in the same manner as it appears on the top of the water. It is preferable that as the bones are simmering, the container is slightly agitated to thus release an optimum amount of the oil from the marrow. Also, it is essential that during this process the bones are always covered in water, which may require adding water to the container ocassionally. It is particularly preferred if at the end of simmering (i.e., after about 30 hours) the bones are agitated to more fully release any remaining lipoidic fraction of the marrow. It is understood that the process described above can be modified, such as for instance waiting until the end of the simmering (i.e. about 30 hours) to collect all of the oily phase at one time.

The oily fraction thus obtained, which becomes a solid upon cooling, is deposited in a sterile container, which may be the container to be marketed, or a container to hold the material for other future use. In any event, the oily composition will have a shelf-life of about 5 years or so, particularly since no water is present. If necessary, any water that may be present in the skimmed off oily substance can be easily removed by further processing, given the fact that the oily phase is not miscible in the aqeous phase and further that oily oily phase solidifies on cooling to ambient temperature. Thus, for example, the oil is allowed to cool after removal from the simmering container, whereby it solidifies and is easily separated or dried of any remaining water.

The composition is believed to contain one or more oils/lipids and proteinaceous materials, as well as other biomolecules. However, the identity of such components has not been determined. It is presumed that proteins have been denatured during the process of heating, and thus any ezymatic activity is lost.

As mentioned previously, the bones may be of any mammalian origin as long as the mammal has hair. Also as mentioned previously, preferred are mammals that are of a domesticated nature. More preferably, the bones are obtained from cows/calves, sheep/lamb, camels, elk, deer, boars and moose. Also preferably, the bones are leg/thigh and hip bones. It is understood, however, that the preferences for sources of bones do not exclude other hairy mammals or other bones in the bodies of the mammals.

In addition, the inventor has found that certain proportions of certain mammalian bones have increased potency (i.e. effectiveness) or are more effective for certain purposes. For instance, hair growth potency can be increased by using certain proportions of certain mammalian bones, and some proportions/sources can be more suited for women in particular or for a certain purpose, such as for eyebrows/eyelashes hair growth. The inclusion of chicken skins along with the bones, for instance, Was found to result in a composition especially well-suited for females. These various formulations are more fully described in the Examples below.

The composition can be used directly in its original form, or can be further processed to formulate it with other agents or in other forms. For instance, the composition may include fragrances, or advantageous agents such as herbal or vitamin components selected for their ability to synergistically enhance treatment and/or delivery through the skin, hair or hair follicles, it being understood that the shelf-life of the combination product may be decreased and thus may require preservative agents as well.

The composition may be also processed into the form of a lotion, gel, cream, foam, aerosol, or other suspension or delivery vehicle, to provide a different product to appeal to an individual's lifestyle. Methods and materials for producing such forms are readily available in the art, such as Remington's Pharmaceutical Sciences, Mack Publishing Co. (A. R. Gennaro edit. 1985), which is specifically incorporated herein by reference. As such, the composition may contain one or more additional chemical compounds or class of chemical compounds therein. It is noted that a treatment composition according to the present invention may include a very wide effective concentration range of the active components in the original lipoidic composition, and the regimen of application in its original form or in combination with other ingredients can be modulated depending on the specific therapeutic or cosmetic goal desired.

Such lotions, gels, creams, etc. may preferably include agents suitable for cleansing the skin and/or hair in the affected, treated area. Such agents include, but are not limited to, soaps, fatty acids, conditioners, and essential oils. Also, suitable thickeners, coloring agents, perfumes, aromatic agents, and/or preservatives may be added to the lotions, gels, creams, or other suspensions or aerosols as desired by the treated individual. Such agents may be useful in disguising or enhancing the color or frangrance of the composition of this invention (although it is noted that the original composition is virtually odorless).

The compositions of the present invention may be formulated for use in conjunction with shampoos, conditioners, styling gels, mousses or other hair care products. For example, the compositions of the present invention may be formulated in conjunction with a shampoo and/or a conditioner to further improve the appearance or apparent thickness of hair.

As used herein, the terms "promote hair growth," and "hair growth promoter", and the like, refer to methods or compositions for increasing the amount of hair growth or restoration of hair growth to the state before the onset of hair loss or hair thinning. As used herein, the terms "prevent hair loss," "hair loss prevention,", and the like, refer to methods or compositions for preventing the degree of hair loss. "Hair loss," as that term is used herein, includes inter alia hair thinning, or regression of terminal hair to vellus hair. "Treating hair loss" means arresting hair loss, reversing hair loss, or both, and promoting hair growth. These phrases refer to any measurable slowing in the rate of hair loss, Which is typically observed by visual inspection.

As used herein, the term "hair" means hair having a terminal hair follicle, including hair on the scalp, transplanted hair, eyebrows and eyelashes. In other words, the compositions and methods are well-suited for terminal hairs. The compositions have no apparent affect if applied to vellus hair, thus one need not be concerned with typical body hair becoming terminal hair in body locations where such would be undesirable.

With regard to the methods of treating hair loss/promoting hair growth, the bone marrow oil composition obtained as described above can be directly applied in a topical manner. There is no particular limitation on the amount of the composition of the present invention to be applied or the regimen of application for treating hair loss. Generally, the composition can be applied to an individual in a dosage of about 10 milligrams to about 1 gram per day of the original, undiluted, composition to the affected area to be treated. In a practical sense, the oily solid is applied in a thin layer to the hair roots. For convenience, the application is performed at night, thus leaving the composition in place with minimal disturbance.

The composition should be applied in such a manner as to ensure it reaches the roots of the hair. That is, when applying for instance to the head, care should be taken to ensure that the composition reaches the scalp and is not just applied to existing hair, in order to achieve the best effect.

As for frequency of application, it is contemplated that the product, in a substantially undiluted form, should be used at least once daily, with positive results being seen in about 10-14 days. However, effective treatment is also possible with a frequency of application of, for example, from a maximum of three to four times daily or even more frequently to once a month or even less frequently. Once positive results are obtained, the frequency of application can be reduced, even substantially, and can be merely modified by the individual in accordance with his/her personal preferences and observations.

Preferably, effective topical treatment appears to be from about once daily to once every three days with the applied composition remaining in place for at least about 15-30 minutes and preferably for a period of about 12-24 hours.

The regimen of usage is determinable by the individual or his/her therapist/cosmetician in light of the cause of the hair loss (a temporary hair loss, due for example to drug exposure, may require only regular use on a temporary basis, until after the removal of the harmful stimulus and subsequent regrowth of hair to a satisfactory level). Male-pattern or age-related baldness of thinning hair, where the causative agent is a constant presence, may require continual application, i.e., the application treatments last for as long as the user is interested in maintaining his or her hair growth.

The effect of the preparation on the hair itself or as an adjunct for skincare may be enhanced by adding various vitamins and other nutrients (vitamin E, etc.) either simultaneously or consecutively. That is, in practicing the methods of the invention, the compositions can be used alone or in combination with other therapeutic or cosmetic agents.

It is specifically to be noted that the present invention essentially requires topical (or external) application of the composition to the skin or hair of a host in need thereof. Such external treatment is contemplated for use of the essential bone marrow oil composition itself. However, since the composition is hot harmful if ingested internally (the oily fraction is normally consumed in soups), internal treatment may be used but only as a supplement to external or topical treatment as set forth above. Specifically, supplemental internal treatment is optional, but not necessary to the invention; internal treatment by itself, on the other hand, is not contemplated as a method of treatment for the compositions of the invention.

As an obvious prerequisite, the methods of the invention contemplate preferably first identifying an individual suffering from hair lass or hair thinning, or one likely to experience hair loss or hair thinning in the future.

The invention also contemplates solving the problem of treating hair transplants in hair transplant patients in order to condition the scalp, promote faster healing of the surgical sites, prevent or reduce hair fall out and prevent or shorten the hair shock time. This problem is satisfactorily solved by the present invention which generally promotes faster graft healing, faster growth of the hair transplants, less itching and less transplant rejection.

With the methods and products of the invention being employed for other purposes, particularly for conditioning the hair shafts and adding body to the hair, it is possible that different application amounts and rates may be determined and desirable. In particular, it may be found that substantially different amounts, probably smaller quantities, may be desirable for hair conditioning. Optimum amounts and frequencies of application can be readily determined by those having ordinary skill in this art.

The present invention is described in more detail in the Examples below. It will be understood by those skilled in the art that the invention is not limited to the specific Examples provided herein. Furthermore, although specific types and amounts of materials and methods of obtaining the bone marrow oil are specified in the following Examples, it will be understood by those skilled in the art that the invention is not limited to these specific amounts and methods, and that variations in the amounts or types of bone marrow starting material, the duration of extraction, and the method of administration, or more specifically, of application to the scalp and/or hair, may be varied and still achieve the desired effect of increasing the amount of hair growth and/or preventing hair loss or hair thinning, and hair conditioning. The invention may be embodied in other specific forms without departing from the spirit or essential characteristics thereof. The present embodiments are to be considered in all respects as illustrative, and not restrictive.

EXAMPLES

Example 1

Preparation of an Essential Bone Marrow Oil Extract Composition for Hair Treatment Ten leg bones of bovine calves were obtained from a butcher, and were cleaned completely of all cartilage, meat and any other material on the outside of the bones and rinsed with water.

The bones were cut to expose the marrow, and immersed completely in a container of water three inches or so above the bones. The water was brought to a boil, and then the heat reduced to a simmer. At about 5 hours post-boiling, with water being added as needed to keep the bones completely immersed throughout, the oil that rose to the top of the container was skimmed off (without also collecting any of the water or minimal amounts of water).

The bones were simmered for an additional 25 hours, during which time the oily fraction that collected on top was removed periodically in the same manner as above. At 30 hours post-boiling, the container was agitated in a back and forth motion, which allowed for additional release of oily material, which also rose to the top and was collected.

The skimmed aliquats of lipiodic material were combined and deposited into sterile containers and sealed.

Example 2

The same process as in Example 1 was carried out, except the bones were obtained from animals in the following proportions:

| Calf Bones: | 8 |
|---|---|
| Mature Cow Bones | 4 |
| Camel Bones | 3 |
| Sheep Bones | 3 |

It was determined that this proportion of mammalian bones resulted in a composition that was about 2× strength (in relation to hair growth treatment) as the base formulation of Example 1.

Example 3

The same process as in Example 1 was carried out, except the bones were obtained from animals in the following proportions:

| Calf Bones | 8 |
|---|---|
| Mature Cow Bones | 4 |
| Camel Bones | 3 |
| Sheep Bones | 3 |
| Large Male Sheep (breeder) Bones | 3 |
| Elk Bones | 3 |
| Deer Bone | 1 |

It was determined that this proportion of mammalian bones resulted in a composition that was about 4× strength as the base formulation of Example 1.

Example 4

The same process as in Example 1 was carried out, except the bones were obtained from animals in the following proportions:

| Calf Bones | 8 |
|---|---|
| Mature Cow Bones | 4 |
| Camel Bones | 3 |
| Sheep Bones | 3 |
| Large Mature Sheep (breeder) bones | 3 |
| Elk Bones | 3 |
| Deer Bones | 1 |
| Wild Boar Bones | 3 |
| Mature Milking Sheep Bones | 3 |
| Large Mature Male Sheep (breeder) | 3 |

It was determined that this proportion of mammalian bones resulted in a composition that was about 6× strength as the base formulation of Example 1.

Example 5

The same process as in Example 1 was carried out, except the bones were obtained from animals in the following proportions:

| | |
|---|---|
| Mature Cow bones | 4 |
| Calf Bones | 8 |
| Camel Bones | 2 |
| Sheep Bones | 2 |
| Deer Bone | 1 |
| Chicken Skins | 10 Kg |

It was determined that this proportion of mammalian bones resulted in a composition that was about 6× strength as the base formulation of Example 1 and particularly suitable for females.

Example 6

The same process as in Example 1 was carried out, except the bones were obtained from animals in the following amounts.

| | |
|---|---|
| Calf Bones: | 10 |
| Elk Bones | 5 |

It was determined that this proportion of mammalian bones resulted in a composition that was particularly suitable for eyebrows and at about 4× strength as the base formulation of Example 1.

Example 7

The same process as in Example 1 was carried out, except the bones were obtained from animals in the following amounts:

| | |
|---|---|
| Calf Bones | 8 |
| Large Cow Bones | 8 |
| Camel Bones | 3 |
| Sheep Bones | 3 |
| Large Male Sheep (Breeder) | 3 |
| Elk Bones | 3 |
| Goat Bones | 3 |
| Moose Bones | 3 |

It was determined that this proportion of mammalian bones resulted in a composition that was particularly suitable for eyebrows and at about 6× strength as the base formulation of Example 1.

Example 8

Testing of the product was carried out on individuals, both men and women. These test subjects employed the treatment product of the invention prepared in accordance with Example 1 for periods of time ranging from as little as several days to several weeks.

The test subjects, at initiation of testing, had a variety of hair conditions ranging from substantially bald through receding hairlines to thinning hair and full heads of hair with varying degrees of hair loss. Hair re-growth in all instances was observed visually on ah average of 10 to 14 days.

The results demonstrate the effectiveness of the treatment product of Example 1.

Example 9

The various treatment products as generally discussed in Examples 2-7 are topically applied in the same manner noted above. In particular, similar topical application is contemplated for various hair conditions and hair locations (e.g., scalp, eyebrows, etc.). In each such application, the treatment composition is topically applied to the area with the particular affliction on a daily basis until hair re-growth is seen, after which the frequency of application is gradually reduced.

I claim:

1. A composition consisting of the lipoidic fractions of the boiled marrow-containing leg bones of bovine calf, bovine cow, camel, sheep, male breeder sheep, elk, deer, wild boar, and mature lactating sheep, the ratio of the boiled marrow-containing leg bones are 8:4:3:3:3:3:1:3:3, by number, respectively and wherein the composition exhibits hair growth promoting properties.

2. A method for treating hair loss in a mammal, comprising topically applying to an affected area of the mammal a composition according to claim 1.

3. The method of claim 2, wherein the affected area is the scalp.

4. The method of claim 2, wherein the affected area is the eyebrows.

5. The method of claim 2, wherein the affected mammal is a human.

6. The method of claim 2, wherein the affected mammal is a domesticated pet.

7. The method of claim 2, wherein the composition is applied daily for a period of at least 10 days.

8. The method of claim 2, in which the composition is applied chronically.

9. A process for preparing a composition according to claim 1, comprising (a) obtaining leg bones of said mammals, (b) cleaning the bones to remove external meat, cartilage and tendons, (c) cutting or breaking the bones such as to expose the bone marrow, (d) immersing the bones completely in a container of water, (e) bringing the water to a boiling stage, and then reducing it to a simmer, and (f) after about five hours, collecting the oily phase that appears on top of the water by skimming it off in a manner ensuring that little or none of the water is collected, thereby obtaining the lipoidic fraction of the marrow-containing bones.

10. The process of claim 8, further comprising, after step (f) continuing to simmer the immersed bones up to about 30 hours post-boiling while periodically collecting said oily phase, and combining them with the oily phase initially collected.

11. The process of claim 9, further comprising agitating the container at the end of the about 30 hour post-boiling point to thereby efficiently release the remaining lipoidic fraction from the simmering bones, collecting this remaining fraction by skimming it from the top of the water, and combining it with the other periodically obtained fractions.

* * * * *